United States Patent [19]

De Boer et al.

[11] 4,136,171

[45] Jan. 23, 1979

[54] ANTIBIOTIC 354 AND PROCESS FOR PRODUCING SAME

[75] Inventors: Clarence De Boer, Kalamazoo; Lester A. Dolak, Plainwell; Durey H. Peterson, Kalamazoo, all of Mich.

[73] Assignee: The Upjohn Company, Kalamazoo, Mich.

[21] Appl. No.: 834,286

[22] Filed: Sep. 19, 1977

[51] Int. Cl.$^2$ .............................................. A61K 35/00
[52] U.S. Cl. .................................. 424/117; 195/80 R
[58] Field of Search ....................... 424/117; 195/80 R

[56] References Cited

U.S. PATENT DOCUMENTS 3,988,441   10/1976   Hawka et al. ........................ 424/117

Primary Examiner—Jerome D. Goldberg
Attorney, Agent, or Firm—Roman Saliwanchik

[57] ABSTRACT

Novel antibiotic 354 (U-54,703) producible in a fermentation under controlled conditions using the new microorganism Streptomyces puniceus subsp. doliceus, NRRL 11160. This antibiotic is active against Gram-negative bacteria, for example, Pseudomonas and Proteus species. Thus, antibiotic 354 can be used in various environments to eradicate or control such bacteria.

9 Claims, 3 Drawing Figures

ANTIBIOTIC 354 AND PROCESS FOR PRODUCING SAME

BACKGROUND OF THE INVENTION

The disclosed fermentation which produces antibiotic 354 also produces the known antibiotic gougerotin. This known antibiotic is described in the publication, JACS 94: 3272 (1972). Gougerotin was also known as aspiculamycin and is disclosed and claimed in U.S. Pat. No. 3,849,398.

BRIEF SUMMARY OF THE INVENTION

Antibiotic 354 is producible in a fermentation under controlled conditions using a biologically pure culture of the new microorganism *Streptomyces puniceus* subsp. *doliceus*, NRRL 11160. Concomitantly produced with antibiotic 354 is the known antibiotic gougerotin. Antibiotic 354 is readily separated from gougerotin during the recovery procedure by subjecting a preparation containing the two antiobiotics to absorption on a cellulose column followed by elution with methanol followed by water. Antibiotic 354 elutes with the methanol and gougerotin elutes with the water.

Antibiotic 354 is active against Gram-negative bacteria, and is especially very active against species of Pseudomonas and Proteus. For example, antibiotic 354 is active against *Pseudomonas aeruginosa* GN-315 (UC 6149) which is resistant to gentamycin, kanamycin and nalidixic acid. Thus, antibiotic 354 can be used to treat topical Pseudomonas infections resistant to gentamycin, kanamycin or nalidixic acid. It can also be used an an oil preservative, for example, as a bacteriostatic agent for inhibiting the growth of *Proteus vulgaris* which is known to cause spoilage in cutting oils. Also, it is useful in wash solutions for sanitation purposes, as in the washing of hands and the cleaning of equipment, floors, or furnishings of contaminated rooms or laboratories; it is also useful as an industrial preservative, for example, as a bacteriostatic rinse for laundered clothes and for impregnating paper and fabrics; and it is useful for suppressing the growth of sensitive organisms in plate assays and other microbiological media. It can also be used as a feed supplement to promote the growth of animals.

DETAILED DESCRIPTION OF THE INVENTION

Chemical and Physical Properties of Antibiotic 354:
Molecular Weight: 172 (field desorption mass. spec.)
Elemental Analysis: $(C_7H_9ClN_2O)_2 \cdot H_2SO_4$ (M.W. 474)
Found: C, 37.08; H, 4.79; N, 12.38; Cl, 15.52; S, 7.48; O, 22.75.

Ultraviolet Absorption Spectrum:
The ultraviolet absorption maxima of antibiotic 354, as reproduced in FIG. 2 of the drawings, are:
In 0.01 N HCl, $\lambda$, a, ($\epsilon$): 213 nm, 38.54, (6,650) and 251 nm, 9.02, (1,550).

Figure 1:
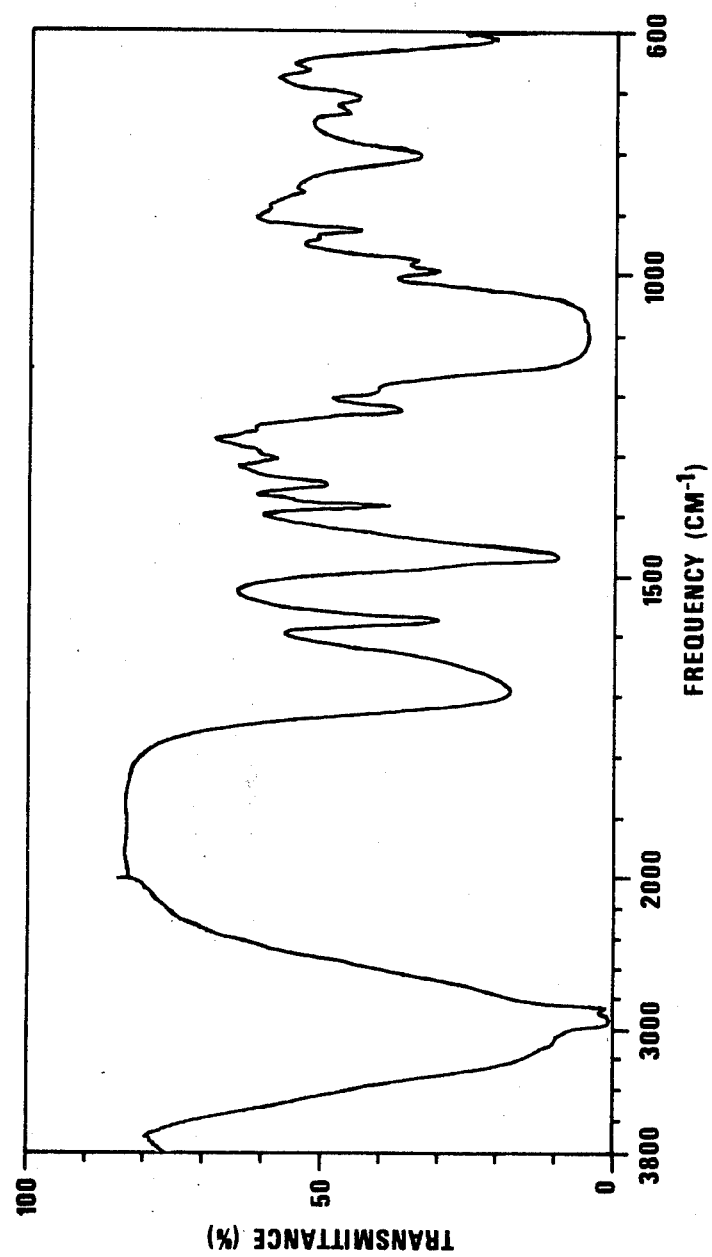

Infrared Absorption Spectrum:
Antibiotic 354, as the sulfate salt, has a characteristic infrared absorption spectrum in a mineral oil mull as shown in FIG. 1 of the drawings. Peaks are observed at the following wave lengths expressed in reciprocal centimeters.
Key: S = Strong M = Medium W = Weak sh = shoulder

| Band Frequency (Wave Numbers) | Intensity |
|---|---|
| 3170 | S (sh) |
| 3070 | S |
| 2950 | S (oil) |
| 2920 | S (oil) |
| 2850 | S (oil) |
| 2750 | S (sh) |
| 1687 | S |
| 1572 | M |
| 1462 | S (oil) |
| 1377 | M (oil) |
| 1342 | M |
| 1300 | W |
| 1285 | W |
| 1252 | W |
| 1217 | M |
| 1187 | M |
| 1100 | S |
| 1062 | S (sh) |
| 992 | M |
| 975 | M |
| 940 | M |
| 925 | M |
| 890 | W |
| 862 | M |
| 800 | M |
| 730 | M |
| 705 | M |
| 660 | M |
| 608 | S |

Solubilities:
Antibiotic 354 is soluble in water, and poorly soluble in methanol, dimethylsulfoxide and dimethylformamide.

Figure 3:
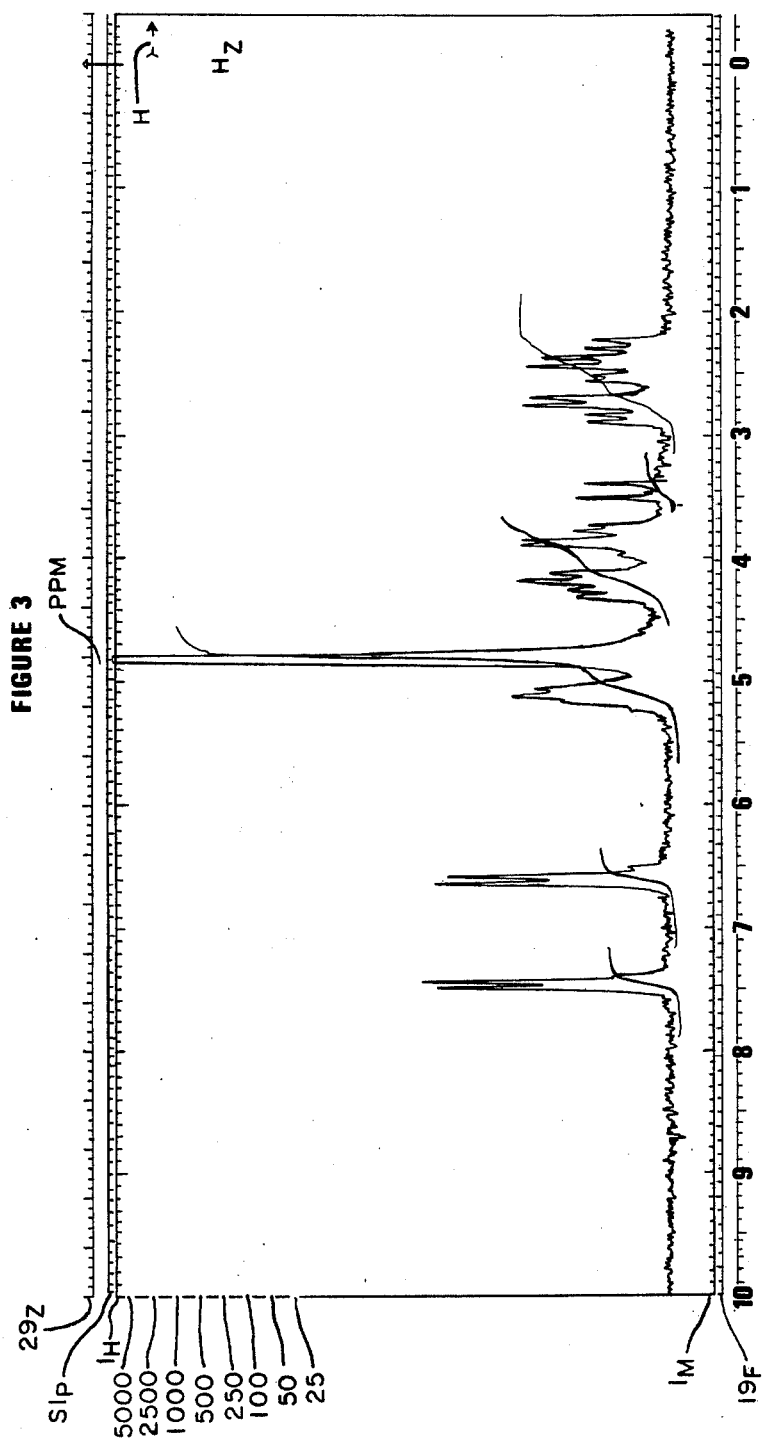

Nuclear Magnetic Resonance (NMR) Spectrum:
The 'H-NMR spectrum of antibiotic 354 (as the sulfate) at 60 megacycles is shown in FIG. 3 of the drawings. The NMR spectrum was observed on a Varian XL-100 Spectrometer on a solution (ca. 0.5 ml., ca. 15% concentration) of the sample of antibiotic 354 in deuterium oxide ($D_2O$). The spectrum was calibrated against external tetramethylsilane and the precision of $\Delta\gamma$ was $> \pm 1$ c.p.s. Frequencies were recorded in c.p.s. downfield from tetramethylsilane.

Antibacterial Spectrum of Antibiotic 354:
Antibiotic 354 shows the following zones of inhibition in millimeters (mm) on a standard disc plate assay (12.7 mm assay discs) at a concentration of 1 mg/ml.

| Microorganism | Zone Of Inhibition |
|---|---|
| *Bacillus subtilis* | 25 mm |
| *Pseudomonas mildenbergii* | 30 mm |

On testing antibiotic 354 by a microplate broth dilution assay using nutrient broth the following spectrum was observed.

| Microorganism | Minimum Inhibitory Concentration (mcg/ml) |
|---|---|
| *Staphylococcus aureus* UC 76 | 31.2 |
| *Streptococcus fecalis* UC 694 | 125 |
| *Escherichia coli* UC 45 | 15.6 |
| *Klebsiella pneumoniae* UC 57 | 31.2 |
| *Klebsiella pneumoniae* UC 58 | 7.8 |
| *Salmonella schottmuelleri* UC 126 | 7.8 |
| *Proteus vulgaris* UC 93 | 15.6 |
| *Proteus mirabilis* | 31.2 |
| *Pseudomonas aeruginosa* UC 95 | 15.6 |
| *Serratia marcescens* UC 131 | 3.9 |
| *Shigella flexneri* UC 143 | 15.6 |
| *Salmonella typhi* | 15.6 |

"UC®" is a registered trademark of The Upjohn Company Culture Collection. These cultures can be obtained from The Upjohn Company in Kalamazoo, Michigan, upon request.

Antibiotic 354 has been shown to be active against *Pseudomonas aeruginosa* strains obtained from Bronson Hospital, Kalamazoo, Michigan. These strains were relatively resistant to the well-known antibiotics kanamycin, gentamycin, nalidixic acid, and Polymyxin B. The results of this comparative test, which was performed on a standard agar disc plate assay using 6.35 mm paper discs with 0.03 ml of antibiotic (1 mg/ml) per disc, follows.

| P. aeruginosa Strain No. | Zones of Inhibition (mm) | | | | |
|---|---|---|---|---|---|
| | Kana- mycin | Genta- mycin | Nalidixic Acid | Polymyxin B | Anti- biotic 354 |
| 6429 | 11 | 14 | 13 | trace | 22 |
| 6430 | 11 | 14 | 13 | trace | 33 |
| 6431 | 0 | trace | 12 | trace | 22 |
| 6433 | trace | 11 | 13 | trace | 21 |
| 6434 | 13 | 22 | 13 | trace | 20 |
| 6435 | 0 | 13 | 17 | trace | 24 |
| 6436 | 0 | 9 | 13 | 9 | 22 |

Antibiotic 354 was also tested on a nutrient broth dilution test against the same Pseudomonas strains listed above. The test tubes were incubated at 32° C. for 18 hours. The results are as follows:

| P. aeruginosa Strain No. | Minimum Inhibitory Concentration (mcq/ml) |
|---|---|
| 6429 | 25 |
| 6430 | 25 |
| 6431 | 25 |
| 6433 | 25 |
| 6434 | 12.5 |
| 6435 | 12.5 |
| 6436 | 25 |

THE MICROORGANISM

The microorganism used for the production of antibiotic 354 and gougerotin is *Streptomyces puniceus* subsp. *doliceus*, NRRL 11160.

A subculture of this microorganism can be obtained from the permanent collection of the Northern Regional Research Laboratory, U.S. Department of Agriculture, Peoria, Ill., U.S.A. Its accession number in this depository is NRRL 11160. It should be understood that the availability of the culture does not constitute a license to practice the subject invention in derogation of patent rights granted with the subject instrument by governmental action.

The microorganism of this invention was studied and characterized by Alma Dietz and Grace P. Li of The Upjohn Research Laboratories.

An actinomycete, isolated from the Upjohn soils screen, was found to be similar in cultural characteristics to the cultures *Streptomyces griseus* var. *purpureus, S. californicus* and *S. vinaceus*. In 1955, Burkholder et al. [Burkholder, P. R. and S. H. Sun, L. E. Anderson, and J. Ehrlich. 1955. The identity of viomycin-producing cultures of Streptomyces Bull. Torrey bot. Cl. 82:108–117], proposed that the viomycin-producing cultures be brought to synonymy in a new variety of *S. griseus* designated *S. griseus* var. *purpureus*. The viomycin-producers are distinguished from *S. griseus* by their distinctive red-purple reverse and pigment on many media [Buchanan, R. E., and N. E. Gibbons. 1974. Bergey's Manual of Determinative Bacteriology, 8th ed. The Williams and Wilkins Co., Baltimore] [Burkholder, P. R., supra] [Shirling, E. B., and D. Gottlieb. 1968. Cooperative description of type cultures of Streptomyces. II. Species descriptions from first study. Int. J. Syst. Bacteriol. 18:69–189][Shirling, E. B., and D. Gottlieb. 1969. Cooperative description of type cultures of Streptomyces. IV. Species descriptions from the second, third and fourth studies. Int. J. Syst. Bacteriol. 19:391–512]. They do not differ from *S. griseus* [Shirling, E. B., and D. Gottlieb. 1968. Cooperative description of type cultures of Streptomyces. III. Additional species descriptions from first and second studies. Int. J. Syst. Bacteriol 18:280–399] in their temperature, carbon utilization, and general growth requirements, or in their spore chain or spore surface pattern.

In 1966, Buchanan et al. [Buchanan, R. E., J. G. Holt, and E. F. Lessel, Jr. 1966. Index Bergeyana. The Williams and Wilkins Co., Baltimore] declared *S. griseus* var. *purpureus* Burkholder et al. an illegitimate name. *S. vinaceus* (Mayer et al.) Waks. and Henrici was also declared illegitimate. *S. californicus, S. floridae* and *S. puniceus* were considered legitimate names. In Bergey's Manual, 8th ed. [Buchanan, R. E., and N. E. Gibbons, supra], the last three named cultures are cited as type cultures. In Shirling and Gottlieb [Shirling and Gottlieb, supra at 18:69–189 and at 19:391–512], *S. californicus, S. puniceus* and *S. vinaceus* are cited as type cultures. The cultural characteristics cited in Burkholder, supra, in Shirling and Gottlieb, supra at 18:69–189, and in Bergey's Manual, 8th ed. [Buchanan, R. E., and N. E. Gibbons, supra] for *S. puniceus* are in agreement with the characteristics noted for the cultures compared with the new soil isolate. Of these cultures, *S. puniceus* Patelski (1950) is the earliest described [Burkholder, P. R., supra]. The new isolate exhibits minor differences in color of growth and antibiotic production from the cultures cited. On the basis of these differences, we propose the designation *Streptomyces puniceus* subsp. *doliceus* subsp. nov. for this new culture.

The methods used were those cited by Dietz [Dietz, A. 1954. Ektachrome transparencies as aids in actinomycete classification. Ann. N. Y. Acad. Sci. 60:152–154] [Dietz, A. 1967. Streptomyces steffisburgensis sp. n. J. Bacteriol. 94:2022–2026], Dietz and Mathews [Dietz, A., and J. Mathews. 1971. Classification of Streptomyces spore surfaces into five groups. Appl. Microbiol. 21:527–533], and Shirling and Gottlieb [Shirling, E. B., and D. Gottlieb. 1966. Methods for characterization of Streptomyces species. Int. J. Syst. Bacteriol. 16:313–340]. *S. puniceus* subsp. *doliceus* was compared with the following viomycin-producing cultures to which it appeared most similar on Ektachrome (Table 1): *S. griseus* var. *purpureus* NRRL 2423 (UC 2414), *S. griseus* var. purpureus CBS (UC 2468), *S. vinaceus* NRRL 2285 (UC 2920), and *S. californicus* ATCC 3312 (UC 5270).

Taxonomy. *Streptomyces puniceus* Finlay & Sobin subsp. *doliceus* Dietz and Li subsp. nov.

Color characteristics. Aerial growth cream to cream pink to lavender-pink. Melanin negative. Appearance on Ektachrome is given in Table 1. Reference color characteristics are given in Table 2. The new culture and *S. californicus* UC 5270 may be placed in the Gray and Violet color groups of Tresner and Backus [Tresner, H. D., and E. J. Backus. 1963. System of color wheels for streptomycete taxonomy. Appl. Microbiol.

11:335-338]; *S. griseus* v. *purpureus* UC 2414 in the Red and Violet color groups; and *S. griseus* v. *purpureus* UC 2468 and *S. vinaceus* UC 2920 in the Gray color group.

Microscopic characteristics. Spore chains long, flexuous (RF) in the sense of Pridham et al. [Pridham, T. G., C. W. Hesseltine, and R. G. Benedict. 1958. A guide for the classification of streptomycetes according to selected groups. Placement of strains in morphological sections. Appl. Microbiol. 6:52-79]. Spore chains may be in tufts. Spores, examined with the scanning electron microscope, are rectangular, appressed, and have a smooth surface which depresses to give a ridged effect.

Carbon utilization. See Tables 3 and 4.

Cultural and biochemical characteristics. See Table 5.

Temperature. All the cultures grew poorly at 18° C., well at 24° C. and very well at 28°-37° C. in 48 hours. There was no growth at 4° C., 45° C. or 55° C. Plates were removed from incubation after 14 days. Plates showing no growth were then incubated at 24° C. All plates from 4° C. showed growth in 24 hours at 24° C.; plates from 45° C. and 55° C. showed no growth with the exception of the plates containing the new culture. This culture grew out from the plates previously incubated at 45° C.

Antibiotic-producing properties. The reference cultures produce the antibiotic viomycin [Burkholder, P. R., supra]. UC 2414 produces the *Bacillus subtilis* and *Klebsiella pneumoniae* activities of the new culture. The new culture produces antibiotic gougerotin and antibiotic 354.

Table 1

Appearance of cultures of Ektachrome*

| Agar Medium | Determination | S. puniceus subsp. doliceus NRRL 11160 | S. griseus var. purpureus NRRL 2423 | S. griseus var. purpureus UC 2468 | S. vinaceus NRRL 2285 | S. californicus ATCC 3312 |
|---|---|---|---|---|---|---|
| Bennett's | S | Lavender-pink | Lavender-pink | Lavender-pink | Lavender-pink | Trace lavender-pink |
|  | R | Red-tan | Red-tan | Red-tan | Red-tan | Red-tan |
| Czapek's sucrose | S | Pale pink | Pink | Pink | Pale Pink | Very slight trace pink |
|  | R | Pale pink | Pink | Pale pink | Pale pink | Pale pink |
| Maltose tryptone | S | Lavender-pink | Lavender-pink | Lavender-pink | Lavender-pink | Very pale pink |
|  | R | Red-tan | Red-tan | Red-tan | Red-tan | Yellow-tan |
| Peptone-iron | S | — | Trace lavender-pink | Trace lavender-pink | Trace lavender-pink | — |
|  | R | Yellow-tan | Yellow-tan | Yellow-tan | Yellow-tan | Yellow-tan |
| 0.1% Tyrosine | S | Pale pink | Pale pink | Pale pink | Pale pink | Trace pale pink |
|  | R | Yellow-tan | Red-tan | Pale pink | Pale pink | Red-tan |
| Casein starch | S | Lavender-pink | Lavender-pink | Lavender-pink | Lavender-pink | Very slight trace pink |
|  | R | Gray-tan | Gray-tan | Gray-tan | Gray-tan | Gray-tan |

S = Surface
R = Reverse
*Dietz, A. 1954. Ektachrome transparencies as aids in actinomycete classification. Ann. N.Y. Acad. Sci. 60:152-154.

Table 2.

Reference Color Characteristics from ISCC-NBS Color Name Charts Illustrated with Centroid Colors*

| Agar Medium | Determination | S. puniceas subsp. doliceus NRRL 11160 | | S.griseus var. purpureus NRRL 2423 | | S. griseus var. purpureus VC 2468 | | S. vinaceus NRRL 2285 | | S. californicus ATCC 3312 | |
|---|---|---|---|---|---|---|---|---|---|---|---|
| | | Chip No. | Color | Chip No. | Color | Chip No. | Color | Chip No. | Color | Chip No. | Color |
| Bennett's | S | 240 | Light reddish purple to | 32 | Grayish yellowish pink | 63 | Light brownish gray | 63 | Light brownish gray | 229 | Dark grayish purple |
| | | 93 | Yellowish gray | | | | | | | | |
| | R | 17 | Very dark red | 21 | Blackish red | 19 | Grayish red | 20 | Dark grayish red | 260 | Very dark purplish red |
| | P | 57 | Light brown | 45 | Light grayish reddish brown | 60 | Light grayish brown | 60 | Light grayish brown | 60 | Light grayish brown |
| Czapek's sucrose | S | 253 | Grayish purplish pink | 253 | Grayish purplish pink | 93 | Yellowish gray | 93 | Yellowish gray | 223 | Moderate purple |
| | R | 253 | Grayish purplish pink | 237 | Strong reddish purple | 93 | Yellowish gray | 244 | Pale purple | 223 | Moderate purple |
| | P | — | — | — | — | — | — | — | — | — | — |
| Maltose tryptone | S | 226 | Very pale purple | 32 | Grayish yellowish pink | 93 | Yellowish gray | 93 | Yellowish gray | 228 | Grayish purple |
| | R | 21 | Blackish red | 17 | Very dark red | 62 | Dark grayish brown | 81 | Dark grayish yellowish brown | 257 | Very deep purplish red |
| | P | 57 | Light brown | 45 | Light grayish reddish brown | 60 | Light grayish brown | 60 | Light grayish brown | — | — |
| Hickey-Tresner | S | 63 | Light brownish gray | 32 | Grayish yellowish pink | 93 | Yellowish gray | 93 | Yellowish gray | 227 | Pale purple |
| | R | 17 | Very | 260 | Very | 259 | Dark | 20 | Dark | 260 | Very dark |

Table 2.-continued

Reference Color Characteristics from ISCC-NBS Color Name Charts Illustrated with Centroid Colors*

| Agar Medium | Determination | S. puniceas subsp. doliceus NRRL 11160 Chip No. | Color | S. griseus var. purpureus NRRL 2423 Chip No. | Color | S. griseus var. purpureus VC 2468 Chip No. | Color | S. vinaceus NRRL 2285 Chip No. | Color | S. californicus ATCC 3312 Chip No. | Color |
|---|---|---|---|---|---|---|---|---|---|---|---|
| | | | dark red | | dark purplish red | | purplish red | | grayish red | | purplish red |
| | P | 57 | Light brown | 45 | Light grayish reddish brown | 60 | Light grayish brown | 60 | Light grayish brown | 60 | Light grayish brown |
| Yeast extract-malt extract (ISP-2) | S | 63 | Light brownish gray | 32 | Grayish yellowish pink | 93 | Yellowish gray | 93 | Yellowish gray | 234 | Dark purplish gray |
| | R | 73 | Pale orange yellow to | 73 | Pale orange yellow to | 73 | Pale orange yellow to | 73 | Pale orange yellow to | 17 | Very dark red |
| | | 21 | Blackish red | 46 | Grayish reddish brown | 46 | Grayish reddish brown | 20 | Dark grayish red | — | — |
| | P | 57 | Light brown | 45 | Light grayish reddish brown | 60 | Light grayish brown | 60 | Light grayish brown | — | — |
| Oatmeal (ISP-3) | S | 240 | Light reddish purple to | 226 | Very pale purple | 63 | Light brownish gray | 93 | Yellowish gray | 257 | Very deep purplish red |
| | | 93 | Yellowish gray | | | | | | | | |
| | R | 242 | Dark reddish purple | 259 | Dark purplish red | 259 | Dark purplish red | 262 | Grayish purplish red | 17 | Very dark red |
| | P | 57 | Light brown | 45 | Light grayish reddish brown | 60 | Light grayish brown | 60 | Light grayish brown | 60 | Light grayish brown |
| Inorganic-salts starch (ISP-4) | S | 63 | Light brownish gray | 32 | Grayish yellowish pink | 93 | Yellowish gray | 93 | Yellowish gray | 227 | Pale purple |
| | R | 242 | Dark reddish purple | 257 | Very deep purplish red | 257 | Very deep purplish red | 259 | Dark purplish red | 21 | Blackish red |
| | P | 57 | Light brown | 45 | Light grayish reddish brown | 60 | Light grayish brown | 60 | Light grayish brown | 60 | Light grayish brown |
| Glycerol-asparagine (ISP-5) | S | 63 | Light brownish gray | 32 | Grayish yellowish pink | 93 | Yellowish gray | 93 | Yellowish gray | 227 | Pale purple |
| | R | 21 | Blackish red | 257 | Very deep purplish red | 257 | Very deep purplish red | 259 | Dark purplish red | 21 | Blackish red |
| | P | 57 | Light brown | 45 | Light grayish reddish brown | 60 | Light grayish brown | 60 | Light grayish brown | 60 | Light grayish brown |

S = Surface
R = Reverse
P = Pigment
*Kelly, K. L., and D. B. Judd. 1955. The ISCC-NBS method of designating colors and a dictionary of color names. U.S. Dept. of Comm. Circ. 553, Washington, D.C.

Table 3

Growth on Carbon Compounds in the Synthetic Medium of Pridham and Gottlieb*

| | S. puniceas subsp. doliceus NRRL 11160 | S. griseus var. purpureus NRRL 2423 | S. griseus var. purpureus UC 2468 | S. vinaceus NRRL 2285 | S. californicus ATCC 3312 |
|---|---|---|---|---|---|
| CONTROL | (+) | (+) | (−) | (+) | (−) |
| 1. D-Xylose | + | + | + | + | + |
| 2. L-Arabinose | (+) | (+) | (+) | (+) | (+) |
| 3. Rhamnose | (+) | (+) | − | (+) | − |
| 4. D-Fructose | + | + | + | + | + |
| 5. D-Galactose | + | + | + | + | + |
| 6. D-Glucose | + | + | + | + | + |
| 7. D-Mannose | + | + | + | + | + |
| 8. Maltose | + | + | + | + | (+) |
| 9. Sucrose | (+) | (+) | (+) | (+) | (+) |
| 10. Lactose | (+) | (+) | (−) | (+) | + |
| 11. Cellobiose | + | + | + | + | + |
| 12. Raffinose | (+) | (+) | (+) | (+) | (−) |

Table 3-continued

| | Growth on Carbon Compounds in the Synthetic Medium of Pridham and Gottlieb* | | | | |
|---|---|---|---|---|---|
| | S. puniceus subsp. doliceus NRRL 11160 | S. griseus var. purpureus NRRL 2423 | S. griseus var. purpureus UC 2468 | S. vinaceus NRRL 2285 | S. californicus ATCC 3312 |
| 13. Dextrin | + | + | + | + | + |
| 14. Inulin | (+) | (+) | (+) | (+) | (−) |
| 15. Soluble Starch | + | + | + | + | + |
| 16. Glycerol | + | + | + | + | + |
| 17. Dulcitol | (+) | (+) | (−) | (+) | (−) |
| 18. D-Mannitol | + | + | + | + | + |
| 19. D-Sorbitol | (+) | (+) | (+) | (+) | (−) |
| 20. Inositol | (+) | (+) | (+) | (+) | (−) |
| 21. Salicin | (+) | (+) | (+) | (+) | (+) |
| 22. Phenol | − | − | − | − | − |
| 23. Cresol | − | − | − | − | − |
| 24. Na Formate | (−) | (−) | − | (−) | − |
| 25. Na Oxalate | (−) | (+) | (+) | (+) | − |
| 26. Na Tartrate | (+) | (+) | (−) | (+) | (−) |
| 27. Na Salicylate | − | − | − | − | − |
| 28. Na Acetate | + | + | + | + | (+)→+ |
| 29. Na Citrate | + | + | + | + | (−) |
| 30. Na Succinate | + | + | + | + | (+) |

+ = Good growth
(+) = Fair growth
(−) = Trace growth
− = No growth
*Pridham, T. G., and D. Gottlieb. 1948. The utilization of carbon compounds by some Actinomycetales as an aid for species determination. J. Bacteriol. 56:107-114.

Table 4

| | Growth of Carbon Compounds in the Synthetic Medium of Shirling and Gottlieb* | | | | |
|---|---|---|---|---|---|
| | S. puniceus subsp. doliceus NRRL 11160 | S. griseus var. purpureus NRRL 2423 | S. griseus var. purpureus UC 2468 | S. vinaceus NRRL 2285 | S. californicus ATCC 3312 |
| Negative Control (Synthetic Medium-ISP-9) | ± | ± | ± | ± | − |
| Positive Control (Synthetic Medium +D-Glucose | ++ | ++ | ++ | ++ | ++ |
| Carbon Compounds: | | | | | |
| L-Arabinose | ± | + | + | ± | + |
| Sucrose | − | − | ± | − | − |
| D-Xylose | ++ | ++ | + | + | ++ |
| Inositol | − | − | − | − | − |
| D-Mannitol | ++ | ++ | ++ | ++ | ++ |
| D-Fructose | + | ++ | + | ++ | ++ |
| Rhamnose | ± | ± | ± | ± | ± |
| Raffinose | − | − | − | − | − |
| Cellulose | − | − | − | − | − |

++ Strong utilization
+ Positive utilization
± Doubtful utilization
− Negative utilization
*Shirling, E. B., and D. Gottlieb. 1966. Methods for characterization of Streptomyces species. Int. J. Syst. Bacteriol. 16:313-340.

Table 5

| Medium | Determination | S. puniceus subsp. doliceus NRRL 11160 | S. griseus var. purpureus NRRL 2423 | S. griseus var. purpureus UC 2468 | S. vinaceus NRRL 2285 | S. californicus ATCC 3312 |
|---|---|---|---|---|---|---|
| Agar | | | | | | |
| Peptone-iron | S | Cream-pink | Pale cream-pink | Cream | Pale cream-pink | Trace cream |
| | R | Yellow-tan | Yellow-tan | Yellow-tan | Yellow-tan | Yellow-tan |
| | P | — | — | — | — | — |
| | O | Melanin negative | Melanin negative | Melanin negative | Melanin negative | Melanin negative |
| Calcium malate | S | Very slight trace cream-pink | Cream | Trace cream | Cream | Trace cream aerial |
| | R | Colorless | Colorless | Colorless | Colorless | Colorless |
| | P | — | — | — | — | — |
| | O | Malate not solubilized | Malate not solubilized | Malate not solubilized | Malate not solubilized | Malate solubilized |
| Glucose asparagine | S | Cream-pink | Cream | Cream | Cream | Cream-pink |
| | R | Maroon center, tan edge | Maroon center, tan edge | Pale pink-red center, cream edge | Pale pink-red center, cream edge | Maroon center, tan edge |

Table 5-continued
Cultural and Biochemical Characteristics

| Medium | Determination | *S. puniceus* subsp. doliceus NRRL 11160 | *S. griseus* var. purpureus NRRL 2423 | *S. griseus* var. purpureus UC 2468 | *S. vinaceus* NRRL 2285 | *S. californicus* ATCC 3312 |
|---|---|---|---|---|---|---|
| Skim milk | P | Pale pink | Pale pink | Pale pink | Pale pink | Pale pink |
|  | S | Very slight trace cream-pink | Cream | Cream | Cream-pink | — |
|  | R | Yellow-tan-orange | Yellow-tan-orange | Yellow-tan-orange | Yellow-tan-orange | Yellow-tan-orange |
|  | P | Yellow-tan-orange | Yellow-tan-orange | Yellow-tan-orange | Yellow-tan-orange | Yellow-tan-orange |
|  | O | Casein solubilized | Casein solubilized | Casein solubilized | Casein solubilized | Casein solubilized |
| Tyrosine | S | Cream | Cream | Cream | Cream | Trace cream |
|  | R | Light tan | Tan | Tan | Tan | Pale yellow |
|  | P | Tan | Tan | Tan | Tan | Pale yellow |
|  | O | Tyrosine solubilized | Tyrosine solubilized | Tyrosine solubilized | Tyrosine solubilized | Tyrosine solubilized |
| Xanthine | S | Cream | Cream | Cream | Cream | Trace cream |
|  | R | Pale cream-tan | Cream-yellow | Cream-yellow | Cream-yellow | Pale yellow |
|  | P | Cream-tan to very pale tan | Cream-yellow to pale tan | Cream-yellow to pale tan | Cream-yellow to pale tan | Very pale yellow |
|  | O | Xanthine not solubilzed | Xanthine not solubilized | Xanthine slightly solubilized | Xanthine not solubilized | Xanthine solubilized |
| Nutrient starch | S | Cream | Cream | Cream | Cream | Trace cream |
|  | R | Pale cream-tan | Cream-yellow | Pale cream-pink-tan | Pale cream-pink-tan | Very pale yellow |
|  | P | None to very pale tan | Cream-yellow to very pale tan | Very pale pink-tan | Very pale pink-tan | — |
|  | O | Starch solubilized | Starch solubilized | Starch solubilized | Starch solubilized | Starch |
| Yeast extract-malt extract | S | Pale lavender with cream edge | Pale lavender with cream edge | Cream with fish-net edge | Cream with fish-net edge | Trace cream |
|  | R | Maroon with tan edge | Maroon with tan edge | Maroon with tan edge | Maroon with tan edge | Pale reddish-tan |
|  | P | Pale red-tan | Pale red-tan | Very pale tan | Very pale tan | Very pale red-tan |
| Peptone-yeast extract-iron (ISP-6) | S | Colorless vegtative | Trace cream aerial on colorless vegetative | White | White | Colorless vegtative |
|  | R | Colorless | Colorless | Yellow-tan | Yellow-tan | Yellow-tan |
|  | P | Trace tan | Trace tan | Yellow-tan | Yellow-tan | Yellow-tan |
|  | O | Melanin negative | Melanin negative | Melanin negative | Melanin negative | Melanin negative |
| Tyrosine (ISP-7) | S | Mottled cream-lavender | Cream | Gray-cream | Gray-cream | Lavender |
|  | R | Maroon | Maroon | Maroon | Maroon | Maroon |
|  | P | Trace pale red-tan | Trace pale red-tan | Gray-pink | Gray-pink | Pale red-tan |
|  | O | Melanin negative | Melanin negative | Melanin negative | Melanin negative | Melanin negative |
| Gelatin Plain | S | Trace white aerial | Trace white aerial | Trace colorless vegetative | Trace white aerial | — |
|  | P | Pale yellow | Pale yellow | Pale yellow | Pale yellow | Pale yellow |
|  | O | Liquefaction ↓ | Liquefactin ↓ | Liquefaction ↓ | Liquefaction ↓ | No liquefaction |
| Nutrient | S | Trace white aerial | Trace white aerial | Trace white aerial | Trace white aerial | — |
|  | P | Yellow | Yellow | Yellow | Yellow | Yellow |
| O | Liquefaction Liquefaction ↓ | Liquefaction ↓ | Liquefaction ↓ | No liquefaction ↓ |  |
| Nitrate Broth Synthetic | S | — | — | — | Cream-pink aerial on lavender-pink vegetative pellicle | — |
|  | P | — | — | — | — | — |
|  | O | Compact bottom growth No reduction Red with Zn dust | Trace bottom growth No reduction Red with Zn dust | Compact bottom growth No reduction Red with Zn dust | Trace bottom growth Reduction | Compact bottom growth No reduction Red with Zn dust |
| Nutrient | S | Cream aerial on maroon ring | Lavender aerial on surface pellicle | Lavender aerial on surface pellicle | Gray-cream aerial on maroon ring | Gray-cream aerial on maroon ring |
|  | P | — | — | — | — | — |
|  | O | Trace bottom growth | Trace bottom growth | Trace bottom growth | Trace bottom growth | Trace bottom growth |

Table 5-continued

| | | Cultural and Biochemical Characteristics | | | | |
|---|---|---|---|---|---|---|
| Medium | Determination | S. puniceus subsp. doliceus NRRL 11160 | S. griseus var. purpureus NRRL 2423 | S. griseus var. purpureus UC 2468 | S. vinaceus NRRL 2285 | S. californicus ATCC 3312 |
| | | No reduction Red with Zn dust | Reduction | Reduction | Reduction | Reduction |
| Litmus Milk | S | Cream aerial on blue vegetative ring | Gray aerial on blue vegetative ring | Gray aerial on blue-gray ring | Gray aerial on blue-gray ring | Trace gray aerial on blue-gray red ring |
| | P | Slight purple | Slight purple | — | — | — |
| | O | Trace peptonization | Trace peptonization | Peptonization | Peptonization | Peptonization good Litmus reduced in one |
| | | pH 7.07 | pH 7.12 | pH 7.3 | pH 7.07 | pH 7.07 |

S = Surface
R = Reverse
P = Pigment
O = Other characteristics

The compounds of the invention process are produced when the elaborating organism is grown in an aqueous nutrient medium under submerged aerobic conditions. It is to be understood, also, that for the preparation of limited amounts surface cultures and bottles can be employed. The organism is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

Production of the compounds by the invention process can be effected at any temperature conducive to satisfactory growth of the microorganism, for example, between about 18° and 40° C., and preferably between about 20° and 28° C. Ordinarily, optimum production of the compounds is obtained in about 3 to 15 days. The medium normally remains acidic during the fermentation. The final pH is dependent, in part, on the buffers present, if any, and in part on the initial pH of the culture medium.

When growth is carried out in large vessels and tanks, it is preferable to use the vegetative form, rather than the spore form, of the microorganism for inoculation to avoid a pronounced lag in the production of the compounds and the attendant inefficient utilization of the equipment. Accordingly, it is desirable to produce a vegetative inoculum in a nutrient broth culture by inoculating this broth culture with an aliquot from a soil, liquid $N_2$ agar plug, or a slant culture. When a young, active vegetative inoculum has thus been secured, it is transferred aseptically to large vessels or tanks. The medium in which the vegetative inoculum is produced can be the same as, or different from, that utilized for the production of the compounds, so long as a good growth of the microorganism is obtained.

A variety of procedures can be employed in the isolation and purification of the compounds produced by the subject invention from fermentation beers, for example, charcoal absorption, 1-butanol extraction, and adsorption on cellulose and cation exchange resins.

In a preferred recovery process the compounds produced by the subject process invention are recovered from the culture medium by separation of the mycelia and undissolved solids by conventional means, such as by filtration or centrifugation.

The antibiotics are then recovered from the filtered or centrifuged broth by absorption on a charcoal column. The charcoal can be eluted by passing 10 to 50% acetone in water (v/v) to remove the antibiotics.

The eluates are pooled and concentrated to an aqueous solution. This solution then is passed over a weak cation exchange resin in the ammonium form, for example, IRC-50 which is supplied by Rohm & Haas, Philadelphia, Pa. The resin can be eluted with an inorganic salt, for example, ammonium chloride, ammonium sulfate (preferred), calcium perchlorate, and the like. Collected fractions are assayed for antibacterial activity as herein described. Fractions showing antibacterial activity can be extracted with 1-butanol to remove impurities. The antibiotics remain in the aqueous phase.

The aqueous phase can be passed over a charcoal column which is then eluted with 25% acetone in water (v/v) and fractions are collected. These fractions are concentrated to an aqueous which is then lyophilized. The next step of the purification process will separate antibiotic 354 from gougerotin.

The lyophilized solid containing antibiotic 354 and gougerotin, described above, is dissolved in a minimum amount of water. This material is injected or layered onto a cellulose column. The column is eluted with methanol and fractions are collected. These fractions contain antibiotic 354. Gougerotin is removed from the cellulose column by eluting the column with water.

Antibiotic 354 is obtained in essentially pure form from the above-described methanol eluates by first concentrating the pooled eluates to a solid and then passing the solid, which has been dissolved in a minimum amount of water, over a strong cation exchange resin, for example, Dowex 50 (supplied by Dow Chemical Co., Midland, Mich.). The column is eluted with a solution of an inorganic salt (ammonium sulfate preferred) and fractions containing essentially pure antibiotic 354 are collected.

Essentially pure gougerotin can be obtained by taking the fractions containing gougerotin from the cellulose column, described above, and passing them over a strong cation exchange resin, as described above for antibiotic 354.

Since antibiotic 354 is a strongly basic compound, procedures involving adsorption on cationic ion exchange resins and elution by organic bases or ammonia can be used to purify crude preparations of antibiotic 354. Also, crude preparations of antibiotic 354 can be purified by transformation to a salt form by treatment with inorganic or organic acids. The base form of the antibiotic can be recovered by neutralization of the acid anion with ammonia or other inorganic or organic bases.

In order to make salts of antibiotic 354 with both inorganic or organic acids, as hereinafter disclosed in exemplary form, it is necessary that the acid be carefully added to an aqueous solution of antibiotic 354 in view of the instability of this antibiotic at acid pH's. Examples of inorganic and organic acids which can be used, but which examples should not be considered limiting, are hydrochloric, sulfuric, phosphoric, acetic, succinic, citric, lactic, maleic, fumaric, pamoic, cholic, palmitic, mucic, camphoric, glutaric, glycolic, phthalic, tartaric, lauric, stearic, salicylic, 3-phenylsalicylic, 5-phenylsalicyclic, 3-methylglutaric, orthiosulfobenzoic, cyclohexanesulfamic, cyclopentanepropionic, 1,2-cyclohexanedicarboxylic, 4-cyclohexenecarboxylic, octadecenylsuccinic, octenylsuccinic, methanesulfonic, benzenesulfonic, helianthic, Reinecke's, dimethyldithiocarbamic, sorbic, monochloroacetic, undecylenic, 4'-hydroxyazobenzene-4-sulfonic, octadecylsulfuric, picric, benzoic, cinnamic, and like acids.

Other procedures for making certain salts are as follows. The sulfate salts can be made by using ammonium sulfate elution from a cation exchange resin. Also, the acetate salts can be made by using pyridinium acetate to elute the antibiotic from cation exchange resins. Further, the chloride salts of antibiotic 354 can be made by using ammonium chloride to elute the antibiotic from a cation exchange resin. The sulfate salts can be converted to the chloride by passing them over an anion exchange resin, for example, Dowex 1 (Cl$^-$) and Dowex 2 (Cl$^-$). If the resin is used in the OH$^-$ form, the free base of 354 is isolated.

The salts of antibiotic 354 can be used for the same biological purposes as the parent antibiotic.

Acylates of antibiotic 354 can be made as follows: A sample of antibiotic 354 is dissolved in an excess of a silylating reagent such as TMS-imidazole or bis-TMS-trifluoroacetamide. A catalyst such as trimethylchlorosilane and/or a base such as pyridine may be used but neither is necessary. An acylating reagent such as trifluoroacetyl-imidazole or acetic anhydride is then added. Acylation is rapid and quantitative as judged by combined gas chromatography-mass spectroscopy. The peaks corresponding to silylated antibiotic 354 (both mono and di-silylated derivatives can be present) disappear and a new one appears with longer retention time and with a mass spectrum indicative of an acylated and monosilylated antibiotic 354. This derivative can then be selectively hydrolyzed with methanol or water to give an acylated derivative of antibiotic 354.

Suitable acid-binding agents include amines such as pyridine, quinoline, and isoquinoline, and buffer salts such as sodium acetate. The preferred base is pyridine. Carboxylic acids suitable for acylation include (a) saturated or unsaturated, straight or branched chain aliphatic carboxylic acids, for example, acetic, propionic, butyric, isobutyric, tertbutylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic aliphatic carboxylic acids, for example, phenylacetic acid, phenylpropionic acid, phenylvaleric acid, cinnamic acid, phenylpropiolic acid, and naphthylacetic acid, and the like. Also, suitable halo-, nitro-, hydroxy-, amino-, cyano-, thiocyano-, and loweralkoxyhydrocarboncarboxylic acids include hydrocarboncarboxylic acids as given above which are substituted by one or more of halogen, nitro, hydroxy, amino, cyano, or thiocyano, or loweralkoxy, advantageously loweralkoxy of not more than six carbon atoms, for example, methoxy, ethoxy, propoxy, butoxy, amyloxy, hexyloxy, and isomeric forms thereof. Examples of such substituted hydrocarboncarboxylic acids are:

mono-, di- and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methylcyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopenanecarboxylic acid;
1-bromo-3,5-dimethylcyclohexanecarboxylic acid;
homogentisic acid, o-, m-, and p-chlorobenzoic acid;
anisic acid;
salicyclic acid;
p-hydroxybenzoic acid;
β-resorcylic acid;
gallic acid;
veratric acid;
trimethoxybenzoic acid;

trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate); and the like.

The above acylates of antibiotic 354 are useful to upgrade the parent compound, i.e. by acylating the parent compound, then removing the acyl group, the parent compound is isolated in a purer form.

Trimethylsilylation of antibiotic 354 gives a volatile di-TMS derivative (along with a little mono-TMS derivative) which is useful in vapor phase chromatography and mass spectroscopy work. This derivative can be prepared by heating a sample of antibiotic 354 at about 60° C. for about 30 minutes in tetrahydrofuran with an excess of bistrimethylsilylacetamide.

Also, the mono-TMS derivative can be prepared using either trimethylsilylimidazole or bistrimethylsilyltrifluoroacetamide. The monosilylated antibiotic 354 can be acylated in situ using trifluoroacetylimidazole, trifluoroacetic anhydride or acetic anhydride. These are also useful in vpc-mass spectroscopic work and represent a practical route to selective (O vs. N) protection of antibiotic 354.

The following examples are illustrative of the process and products of the invention, but are not to be construed as limiting. All percentages are by weight and all solvent mixture proportions are by volume unless otherwise noted.

EXAMPLE 1

A. Fermentation

A biologically pure culture of *Streptomyces puniceus* subsp. *doliceus*, NRRL 11160, is used to inoculate 500-ml Erlenmeyer seed flasks containing 100 ml of sterile medium consisting of the following ingredients:

| | |
|---|---|
| Glucose | 10 g/l |
| Yeast Extract | 2.5 g/l |
| Peptone | 10 g/l |
| Deionized Water q.s. | 1 liter |

The seed medium presterilization pH is 6.5. The seed inoculum is grown for three days at 28° C. on a Gump rotary shaker operating at 250 r.p.m. Seed inoculum, prepared as described above, is used to inoculate 500-ml Erlenmeyer fermentation flasks containing 100 ml of sterile fermentation medium consisting of the following ingredients:

| | |
|---|---|
| Brer Rabbit/Sucrest* | 20 ml/l |
| Yeast Extract/Brewer's Yeast** | 2 g/l |
| Dextrin*** | 10 g/l |
| Cerelose*** | 15 g/l |
| Proteose-Peptone #3** | 10 g/l |
| Peanut Meal | 5 g/l |
| Water q.s. | 1 liter |

*RJR Foods, Inc., New York, NY
**Difco Laboratories, Detroit, MI
***CPC International, Inc., Englewood Cliffs, NJ The presterilization pH is 7.0. The fermentation flasks are inoculated at the rate of 5 ml of seed inoculum per 100 ml of fermentation medium. The fermentation flasks are grown for 3 days at a temperature of 25°–28° C. on a Gump rotary shaker operating at 250 r.p.m.

A representative shake flask fermentation harvested after 3 days shows the following assay pattern against *Pseudomonas mildenbergii* (UC 3029).

| Day | Assay Results (BU/ml) |
|---|---|
| 1 | 0 |
| 2 | 14 |
| 3 | 14 |

The assay is an agar disc plate assay using the microorganism *P. mildenbergii*. The agar medium is buffered with 0.1 M phosphate buffer at a pH of 7.4. A unit volume (0.08 ml) of solution containing the substance to be assayed is placed on a 12.7 mm paper disc which is then placed on an agar plate seeded with the assay organism. The agar plate is then incubated for 16–18 hours at 37° C. A biounit (BU) is defined as the concentration of the antibiotic which gives a 20 mm zone of inhibition under the above assay conditions. Thus, if for example a fermentation beer, or other solution containing the antibiotic, needs to be diluted 1/100 to give a 20 mm zone of inhibition, the potency of such beer or solution is 100 BU per ml.

B. Recovery (1) Carbon Sorption

Ten liters of shake flask-grown beer, as described above, is stirred with 4 l washed, granular charcoal for 15 minutes. The charcoal is allowed to settle for 10 minutes and the beer is decanted. The charcoal is washed with deionized water until the water remains clear. An overhead paddle stirrer is used in the first step and a 10 l pail in the second step. The charcoal is slurried into a chromatography tube with deionized water. The activities are eluted with 25% acetone in water using gravity flow at the highest possible flow rate. One liter fractions are collected until a yellow color emerges. When the yellow color is almost undetectable small fractions are again collected. The yellow fractions (11 l) are concentrated to an aqueous at 35°–40° C./1 mm and assayed. The data are presented in Table I below. It is seen that 80% of the UC 3029 biounits are recovered from the column.

Table I

| Sample | Volume | Dilution | Pseudomonas Mildenbergii (UC 3029) | Bacillus subtilis | Conc. | BU/mg |
|---|---|---|---|---|---|---|
| Whole Beer | 10 l | FS* | 28 mm | 24 mm | — | — |
| | | 1:2 | 23 | 21 | — | — |
| | | 1:4 | trace | 20 | — | — |
| | | 1:8 | NZ** | 19 | — | — |
| Spent Beer | 11 l | FS | NZ | 20 | — | — |
| 1st Eluate | 3 l | FS | NZ | — | — | — |
| 2nd Eluate | 9 l | FS | 25 | — | — | — |
| 3rd Eluate | 2 l | FS | NZ | — | — | — |

Table I-continued

| Sample | Volume | Dilution | Pseudomonas Mildenbergii (UC 3029) | Bacillus subtilis | Conc. | BU/mg |
|---|---|---|---|---|---|---|
| Aqueous Pool | 8 l | FS | 29 | 23 | 16.9 mg/ml | 0.18 |
|  |  | 1:2 | 23 | 19 | (3 BU/ml) |  |
|  |  | 1:4 | 16 | trace |  |  |

FS* = Full Strength
NZ** = No Zone (2) IRC-50 Sorption

Carbon eluates from four runs (about 48 l of beer in all), as described above, are pooled to give 33 l of aqueous which assay for a total of 91,000 UC 3029 biounits. This is passed over 2 pounds of IRC-50 ($NH_4^+$) in a chromatography tube at 5–6 l/hour. The column is then washed with 4 l of deionized water and eluted with 1 M $(NH_4)_2SO_4$ solution. The fractions are assayed by UV after diluting them 1:10 with water. On the basis of the UV data, the first two eluates are pooled. The third eluate is saved. The data are presented in Table II below.

Table II

| Sample | Volume | Pseudomonas mildenbergii (UC 3029) | Bacillus subtilis | A | λ |
|---|---|---|---|---|---|
| Spent | 33.4 l | NZ | NZ | 1.4 | 265 nm |
| Wash | 3.5 l | NZ | NZ | 0.24 | 265 |
| 1st Eluate | 320 ml | 21 mm | 20 mm | 0.62 | 265 |
| 2nd Eluate | 2000 ml | 31 | 30 | 5.80 | 260 |
| 3rd Eluate | 2000 ml | 23 | 20 | 2.18 | 255 |
| 4th Eluate | 1000 ml | 18 | NZ | 1.29 | 255 |
| 5th Eluate | 1000 ml | NZ | NZ | 1.13 | 255 |

(3) Desalting

Eluate #3 above (2000 ml) is passed over 200 ml granular charcoal in a chromatography tube. The column is washed with 500 ml deionized water. Neither the spent nor the wash has any UV absorbance. The activities are eluted with 700 ml 25% acetone in water. The eluate is concentrated to an aqueous amounting to 500 ml. A 1:10 dilution of this absorbs strongly at 255 nm. Bioautography on cellulose with methanol shows that gougerotin and antibiotic 354 are present.

(4) Ultrafiltration

The desalted aqueous from above is passed over an Amicon UM 2 ultrafilter (Amicon Corp., 21 Hartwell Avenue, Lexington, MA 02173). The retentate shows no activity and is discarded after a wash of one volume. The first filtrate and wash are pooled and lyophilized. The residue weights 4.5 gm. This shows a UV max at 252 nm with an inflection at 212 nm on a strong end absorption.

(5) Separation of Gougerotin From Antibiotic 354

A 68 gm preparation treated essentially as described above (except for the ultrafiltration), assays at 0.68 BU/mg vs. *B. subtilis;* it is labeled Prep. 216-4. Bioautography shows that it contains gougerotin and antibiotic 354.

A cellulose 300 column measuring 5.0 × 150 cm is flushed with methanol at 20 ml/minute (10 psi). The bed volume is 2.9 l.

Thirty grams of the above Prep. 216-4 is dissolved in 65 ml water and the solution is injected onto the column. Some of the solid precipitates when it contacts the methanol but this does not plug the column or otherwise interfere with the procedure. The column is eluted with methanol at 20 ml/minute. The eluate fractions are assayed by UV using 1:10 dilutions. The data are presented in Table III. Fractions 3–8 are pooled and concentrated to give 10.2 gm tan solid. Bioautography shows this to contain antibiotic 354 and no gougerotin. A second injection using the rest of the sample and similarly analyzed yields 12.0 gm of a like preparation.

Table III

| Fraction | Volume | Color | $A_{255-265}$ | Pseudomonas mildenbergil (UC 3029) |
|---|---|---|---|---|
| 1 | 1300 ml | Colorless | 0.00 | — |
| 2 | 1200 ml | Colorless | 0.21 | — |
| 3 | 400 ml | Colorless | 2.13 | 30 mm |
| 4 | 400 ml | Light Yellow | 9.30 | 40 |
| 5 | 425 ml | Light Yellow | 12.8 | 39 |
| 6 | 500 ml | Light Yellow | 12.4 | 36 |
| 7 | 500 ml | Trace Yellow | 8.4 | 27 |
| 8 | 500 ml | Colorless | 1.12 | 23 |
| 9 | 500 ml | Colorless | — | 20 |
| 10 | 500 ml | Colorless | — | 19 |
| 11 | 500 ml | Colorless | — | trace |

After fraction #11 the solvent is switched to water and the elution is continued at 20 ml/minute. The data are presented in Table IV below. Fractions 2 and 3 are pooled and lyophilized to give 17.9 gm tan solid. A second injection yields 22.1 gm. Bioautography shows this to contain only gougerotin.

Table IV

| Fraction | Volume | Color | $A_{269}$ |
|---|---|---|---|
| 1 | 1000 ml | Colorless | 0.30 |
| 2 | 1000 ml | Yellow | 11.0 |
| 3 | 900 ml | Light Yellow | 2.64 |
| 4 | 1400 ml | Colorless | 0.08 |

The 68 gm sample (216-4) gives 22.2 gm (32.6%) antibiotic 354-containing solids and 40 gm (58.8%) gougerotin-containing solids.

The 22 gm of antibiotic 354 material assays at 0.35 BU/mg vs. B. subtilis and 0.83 BU/mg vs. UC 3029.

The 22 gm of gougerotin material obtained from the second run assays at 0.5 BU/mg vs. B. subtilis and 1.5 BU/mg vs. UC 3029.

Both preparations are grossly impure.

(6) Pure Gougerotin

A pool from two cellulose runs similar to that described above (but ultrafiltered) amounts to 5.8 gm. This is dissolved in 15 ml water and injected onto a 200–400 mesh Amberlite CG-120 ($NH_4^+$) column (Rohm & Haas, Philadelphia, Pa.) measuring 2.5 × 100 cm. This is eluted with a water to 1 M $(NH_4)_2SO_4$ gradient at 12 ml/minute.

Fractions amounting to 25 ml are collected. Every fifth fraction is assayed (100 λ/12.7 mm pad) vs. UC 3029. There is no activity through tube #250. The UV assay is done with 1:10 dilutions of every tenth tube. This shows no 265 nm band through tube #250. The UV data for subsequent tubes is presented in Table V. The *B. subtilis* zones obtained for tubes 260–370 are very small. Tubes 280-340 are pooled to give 1.4 l solution. This is desalted over 200 ml charcoal in a chromatography tube. The charcoal is washed with water and eluted with 25% acetone in water. The fractions are monitored by UV absorbance at 268 nm. The aqueous eluate is lyophilized to give 1.0 gm of essentially pure gougerotin as a white solid.

Table V

| Fraction | $A_{268}$ | Fraction | $A_{268}$ |
|---|---|---|---|
| 260 | 0.26 | 320 | 1.87 |
| 270 | 0.27 | 330 | — |
| 280 | 0.45 | 340 | 0.68 |
| 290 | 1.30 | 350 | 0.32 |
| 300 | 2.46 | 360 | 0.20 |
| 310 | 2.55 | 370 | 0.15 |

(7) Pure Antiobiotic 354 As The Sulfate

A pool is made of various fractions which had been treated as described above through the cellulose column step. It amounts to 3.78 gm and is dissolved in 10 ml water. This is injected onto the CG-120 ($NH_4^+$) column described above for gougerotin and eluted with the same gradient at the same rate. An aliquot of every tenth tube is diluted 1:10 with water and examined by UV and dioassayed. Nothing elutes up to tube #220. The data for subsequent tubes are presented in Table VI. Fractions 248-340 are pooled to give 2.5 l solution with $A_{252} = 1.27$. This is desalted as described for gougerotin using a bed of charcoal measuring 3.5 × 28 cm (270 ml) and monitoring at the appropriate wavelengths. The desalted eluate is lyophilized to give 2.36 gm essentially pure antibiotic 354 as a tan solid. It assays at 8 BU/mg vs. UC 3029.

Table Vi

| Fraction | $A_{255}$ | $A_{212}$ | Pseudomonas mildenbergil (UC 3029) |
|---|---|---|---|
| 230 | 0.23 | 1.08 | — |
| 240 | 1.10 | 5.39 | — |
| 250 | 1.60 | 8.20 | — |
| 260 | 1.87 | 8.60 | 35 mm |
| 270 | 2.75 | 10.1 | 40 |
| 280 | 2.05 | 9.00 | 39 |
| 290 | 1.49 | 6.95 | 37 |
| 300 | 1.03 | 4.60 | 33 |
| 310 | 0.69 | 2.41 | 26 |
| 320 | 0.46 | 1.88 | NZ |
| 330 | 0.31 | 1.25 | NZ |
| 340 | 0.20 | 0.82 | NZ |
| 350 | 0.15 | 0.51 | NZ |

EXAMPLE 2

Acetylation Of Antibiotic 354

A sample of antibiotic 354 is stirred in tetrahydrofuran with pyridine and acetic anhydride. The solvent is removed in vacuo and the residue is partitioned between ethyl acetate and 0.01 N HCl. The aqueous is lyophilized. When the solids are redissolved in water, crystals form and are collected. These crystals are shown by mass spectroscopy to be the mono-N-acetyldehydrochlorinated derivative of antibiotic 354.

EXAMPLE 3

Preparation Of Antibiotic 354.HCl From Antibiotic 354.H$_2$SO$_4$

A 14 mg sample of antibiotic 354.H$_2$SO$_4$ is dissolved in 0.3 ml water and passed over a 0.4 × 8 cm column of 100-200 mesh Dowex 2 × 8 (Cl$^-$). Eluted with distilled water and assayed each 3.0 ml fraction with ninhydrin spray after spotting onto a cellulose tlc (thin layer chromatography) plate and by UV absorption (bands at 251 and 211 in a 1:4 ratio). The appropriate pool is lyophilized. The solid residue is judged to be the hydrochloride by mass spectroscopy.

EXAMPLE 4

Preparation Of Antibiotic 354.HOAc From A Mix Of Gougerotin And Antibiotic 354

An aqueous carbon eluate (4 l) containing gougerotin and antibiotic 354 is passed over a column of 200 g Dowex 50 W × 8 (H$^+$). The column is washed with deionized water and eluted with 2.0 M pyridinium acetate buffer at pH 5. Fractions 13-17 (45 ml each) are pooled on the basis of bioactivity (12.7 mm pads, agar tray) vs. UC 3029 an lyophilized. The solids give bioautographic patterns indicating that the main activity is antibiotic 354 which must be in the acetate form. The mixture of acetates so obtained is separated into gougerotin acetate and antibiotic 354 acetate by cellulose chromatography as described above.

Figure 2:
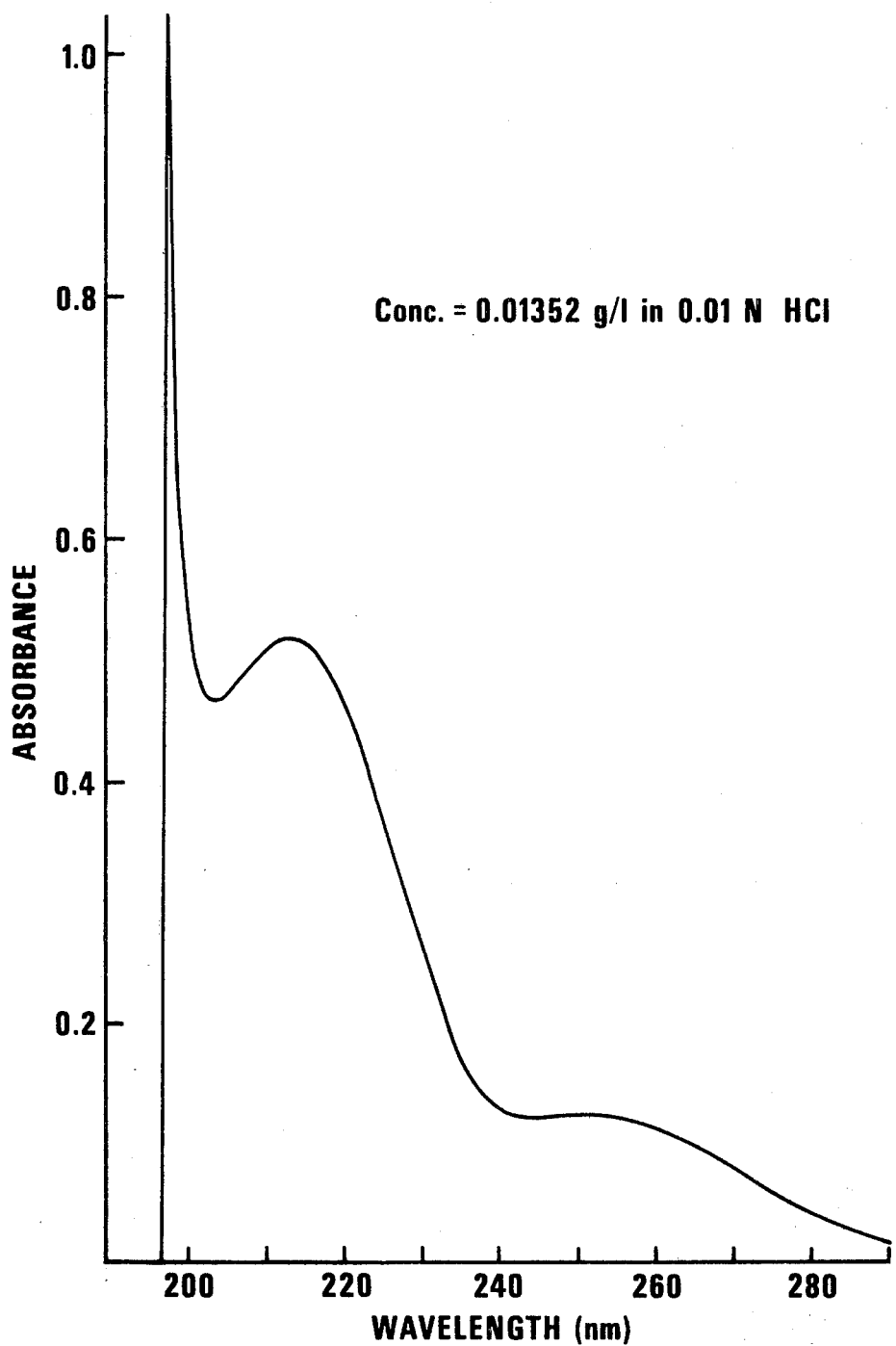

We claim:

1. Antibiotic 354 which is active against Pseudomonas and Proteus and which in its essentially pure form is characterized as the sulfate salt having the following characteristics:

a. molecular weight of 172 (field desorption mass. spec.);
  b. has the following elemental analysis: C, 37.08; H, 4.79; N, 12.38; Cl, 15.52; S, 7.48; O, 22.75;
  c. is soluble in water and relatively insoluble in methanol, acetone, dimethylsulfoxide and dimethylformamide;
  d. has a characteristic infrared absorption spectrum when dissolved in a mineral oil mull as shown in FIG. 1 of the drawings;
  e. has a characteristic ultraviolet absorption spectrum as shown in FIG. 2 of the drawings; and,
  f. has a characteristic NMR spectrum as shown in FIG. 3 of the drawings.

2. Acid addition salts of antibiotic 354, said antibiotic having the physical and chemical characteristics as defined in claim 1.

3. Antibiotic 354 sulfate salt, a compound according to claim 2.

4. Antibiotic 354 hydrochloride salt, a compound according to claim 2.

5. Antibiotic 354 acetate salt, a compound according to claim 2.

6. Mono-N-acetyldehydrochlorinated derivative of antibiotic 354, said antibiotic having the physical and chemical characteristics as defined in claim 1.

7. Trimethylsilyl derivative of antibiotic 354, said antibiotic having the physical and chemical characteristics as defined in claim 1.

8. A process for preparing antibiotic 354, as defined in claim 1, which comprises cultivating Streptomyces puniceus subsp. doliceus, having the identifying characteristics of NRRL 11160, in an aqueous medium under aerobic conditions until substantial antibiotic 354 activity is imparted to said medium.

9. A process, according to claim 8, wherein said aqueous nutrient medium contains a source of assimilable carbohydrate and assimilable nitrogen.

* * * * *

UNITED STATES PATENT AND TRADEMARK OFFICE
CERTIFICATE OF CORRECTION

PATENT NO. : 4,136,171           Page 1 of 2

DATED : January 23, 1979

INVENTOR(S) : Clarence DeBoer, Lester A. Dolak, and Durey H. Peterson

It is certified that error appears in the above–identified patent and that said Letters Patent are hereby corrected as shown below:

Column 1, line 20, for "antiobiotics" read -- antibiotics --.
Column 6, Table 1, line 1, for "of Ektachrome" read -- on Ektachrome --. Columns 5-6, Table 2, line 3, for "S. puniceas" read -- S. puniceus --; line 6, for "VC 2468" read -- UC 2468 --. Columns 7-8, Table 2, line 3, for "S. puniceas" read -- S. puniceus --; line 6, for "VC 2468" read -- UC 2468 --. Columns 9-10, Table 4, line 12, for " + D-Glucose" read -- + D-Glucose) --. Columns 11-12, Table 5, line 28, for "Xanthine not solubilzed" read -- Xanthine not solubilized --; line 37, for "Starch" read -- Starch solubilized --; line 46, for "Colorless vegtative" read -- Colorless vegetative --; again for "Colorless vegtative" read -- Colorless vegetative --; line 71, for " Nutrient 0     Li- Liquefaction Liquefaction Liquefaction No
             quefaction                                  liquefaction"

read -- Nutrient
        0 Liquefaction Liquefaction Liquefaction Liquefaction No
                                                              liquefaction--

UNITED STATES PATENT AND TRADEMARK OFFICE
CERTIFICATE OF CORRECTION

PATENT NO. : 4,136,171
DATED : January 23, 1979
INVENTOR(S) : Clarence DeBoer, Lester A. Dolak, and Durey H. Peterson It is certified that error appears in the above-identified patent and that said Letters Patent are hereby corrected as shown below:

Column 16, line 59, for "3-bromo-2,2,3-trimethylcyclopenane-" read -- 3-bromo-2,2,3-trimethylcyclopentane --.
Column 21, line 34, for "Table Vi" read -- Table VI --.
Column 22, line 16, for "an" read -- and --. Column 22, Claim 8, line 61, for "aqueous medium" read -- aqueous nutrient medium --.

Signed and Sealed this

Twenty-ninth Day of May 1979

[SEAL]

Attest:

RUTH C. MASON
Attesting Officer

DONALD W. BANNER
Commissioner of Patents and Trademarks